United States Patent [19]
Teshima et al.

[11] Patent Number: 6,043,397
[45] Date of Patent: Mar. 28, 2000

[54] METHOD FOR PRODUCTION OF FLUORINE-CONTAINING AROMATIC COMPOUNDS

[75] Inventors: Seiichi Teshima, Toride; Yoshinobu Asako, Tsuchiura, both of Japan

[73] Assignee: Nippon Shokubai Co., Ltd., Japan

[21] Appl. No.: 09/139,422

[22] Filed: Aug. 25, 1998

[30] Foreign Application Priority Data

Aug. 29, 1997 [JP] Japan ................................. 9-235149

[51] Int. Cl.$^7$ .......................... C07C 19/08; C07C 25/13; C07C 47/52; C07C 47/546
[52] U.S. Cl. .......................... 568/425; 568/437; 568/439; 568/440; 570/127; 570/143; 570/147
[58] Field of Search ..................... 570/127, 143, 570/147; 568/425, 437, 439, 440

[56] References Cited

U.S. PATENT DOCUMENTS

| | | | |
|---|---|---|---|
| 2,859,245 | 11/1958 | Smith et al. | 260/544 |
| 3,914,265 | 10/1975 | Middleton | 260/397.3 |
| 3,976,691 | 8/1976 | Middleton | 260/544 |

OTHER PUBLICATIONS

Markovskii et al., "Application of dialkylaminosulfur trifluorides inteh synthesis of fluoroorganic compounds", Synthesis (SYNTBF); 73; (12); pp. 787–789, XP002085446 Inst. Org. Chem.; Kiev; USSR (1973).

Hasek et al., "The Chemistry of Sulfur Tetrafluoride. II The Fluorination of Organic Carbonyl Compounds", J.Amer.Chem.Soc., 82:543–551 (1960).

*Primary Examiner*—Johann Richter
*Assistant Examiner*—Jane C. Oswecki
*Attorney, Agent, or Firm*—Fish & Richardson P.C.

[57] ABSTRACT

A method for the production of a fluorine-containing aromatic compound is provided which allows the relevant reaction to proceed in a standard reaction vessel such as, for example, a glass vessel at room temperature under an ambient pressure without requiring provision of such special devices as have been necessary heretofore or adoption of harsh reaction conditions. This method comprises causing an aromatic compound (A) having a cyclic skeletal part of 6 to 16 carbon atoms containing a plurality of —C(=O)X groups, wherein X stands for a hydrogen atom, a halogen atom, or an alkyl group of 1 to 10 carbon atoms, and having the remaining hydrogen atoms unsubstituted or partly or wholly substituted with at least one species of halogen atom to react with a compound (B) represented by the formula:

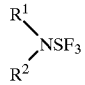

wherein $R^1$ and $R^2$ independently stand for an alkyl group of 1 to 6 carbon atoms or a phenyl group.

10 Claims, No Drawings

METHOD FOR PRODUCTION OF FLUORINE-CONTAINING AROMATIC COMPOUNDS

BACKGROUND OF THE INVENTION

1. Field of the Invention

This invention relates to a method for the production of a fluorine-containing aromatic compound which is useful as a raw material for a resin excelling in various properties such as, for example, heat-resistance, chemical-resistance, and water-repellency.

2. Description of the Related Art

It has been heretofore known that a fluorine-containing aromatic compound having a fluoroalkyl group is useful as a raw material for a resin excelling in various properties such as, for example, heat-resistance, chemical-resistance, and water-repellency. Methods for the production of such a fluorine-containing aromatic compound have been known in two types, i.e., the reaction of aldehyde with sulfur tetrafluoride ($SF_4$) [J. Am. Chem. Soc., 82, pp. 543–551 (1960)] and the halogen-exchanging reaction with a dihalomethyl group-containing compound.

The former method relying on the reaction of aldehyde with sulfur tetrafluoride, however, requires provision of a special equipment including a reaction vessel excelling in heat-resistance, pressure-resistance and corrosion-resistance, such as a vessel formed of Hastelloy, a stainless steel alloy (Ni—Mo type), because sulfur tetrafluoride has strong toxicity and corrosiveness and the reaction of terephthalaldehyde with sulfur tetrafluoride, for example, must be carried out under such harsh conditions as high temperature and high pressure like 150° C. and 80 MPa. The former method, therefore, not only suffers an undue rise in the cost of production of a fluorine-containing aromatic compound but also entails the problem of a high risk in view of the production using a highly corrosive fluorinating agent at a high temperature under a high pressure and of allowing no easy commercialization of the production.

The latter method relying on the halogen-exchanging is at a disadvantage in attaining halogen-exchange of a compound having a plurality of dihalomethyl groups only with extreme difficulty because the reaction is generally required to be carried out at a high temperature and the yield of production is low.

SUMMARY OF THE INVENTION

An object of this invention is to provide a method for the production of a fluorine-containing aromatic compound which can be carried out in a standard reaction vessel such as, for example, a vessel made of glass at room temperature under normal pressure unlike a conventional method which requires provision of a special equipment or use of harsh reaction conditions.

Another object of this invention is to provide a method for the production of a fluorine-containing aromatic compound which is capable of producing a fluorine-containing aromatic compound having a fluoroalkyl group at low costs.

The objects mentioned above can be accomplished by a method for the production of a fluorine-containing aromatic compound which comprises causing an aromatic compound (A) having a cyclic skeletal part of 6 to 16 carbon atoms containing a plurality of —C(=O)X groups (wherein X stands for a hydrogen atom, a halogen atom, or an alkyl group of 1 to 10 carbon atoms) and having the remaining hydrogen atoms unsubstituted or partly or wholly substituted with at least one species of halogen atom to react with a compound (B) represented by the formula:

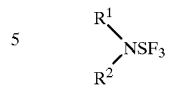

wherein $R^1$ and $R^2$ independently stand for an alkyl group of 1 to 6 carbon atoms or a phenyl group.

The above and other objects, features and advantages of the present invention will become clear from the following description of the preferred embodiments.

The method of this invention can be carried out in a standard reaction vessel such as a vessel made of glass at room temperature under an ambient pressure unlike a conventional method which requires provision of a special equipment or use of harsh reaction conditions. Thus, it allows the production of a fluorine-containing aromatic compound useful as a raw material for a resin excelling in various properties such as heat-resistance, chemical-resistance, and water-repellency at low costs.

DETAILED DESCRIPTION OF THE PREFERRED EMBODIMENT(S)

The method for the production of a fluorine-containing aromatic compound of this invention is characterized by causing an aromatic compound (A) having a cyclic skeletal part of 6 to 16 carbon atoms containing a plurality of —C(=O)X groups (wherein X stands for a hydrogen atom, a halogen atom, or an alkyl group of 1 to 10 carbon atoms) and having the remaining hydrogen atoms unsubstituted or partly or wholly substituted with at least one species of halogen atom to react with a compound (B) represented by the formula:

wherein $R^1$ and $R^2$ independently stand for an alkyl group of 1 to 6 carbon atoms or a phenyl group.

The aromatic compound (A) to be used in this invention (hereinafter occasionally referred to simply as "compound (A)") is a compound which possesses a cyclic skeletal part of 6 to 16 carbon atoms containing a plurality of —C(=O)X groups (wherein X stands for a hydrogen atom, a halogen atom, or an alkyl group of 1 to 10 carbon atoms) and having the remaining hydrogen atoms destitute of —C(=O)X group unsubstituted or partly or wholly substituted with at least one species of halogen atom.

The cyclic skeletal part of such a compound (A) is not particularly restricted so far as the carbon atoms thereof be in the range of 6 to 16. As typical examples thereof, benzene, biphenyl, phenyl ether, indene, indan, naphthalene, 1,4-dihydronaphthalene, tetralin, biphenylene, acenaphthylene, acenaphthene, fluorene, phenanthrene, anthracene, fluoranthene, aceanthrene, pyrene, 1-phenyl naphthalene, and 2-phenyl naphthalene may be cited. Among other examples of the cyclic skeletal parts of the compound (A) cited above, those having a continuous conjugated system such as, for example, benzene, biphenyl, naphthalene, biphenylene, acenaphthylene, phenanthrene, anthracene, fluoranthene, pyrene, 1-phenyl naphthalene, and 2-phenyl naphthalene are favorably used and benzene, naphthelene, biphenyl, phenyl ether, and anthracene are particularly favorably used.

The compound (A) contains a plurality of —C(=O)X groups. In this group, X represents a hydrogen atom, a halogen atom such as, for example, fluorine, chlorine, bromine, or iodine, preferably fluorine, chlorine, or bromine, and more preferably fluorine, or an alkyl group of 1 to 10 carbon atoms such as, for example, methyl, ethyl, n-propyl, isopropyl, n-butyl, tert-butyl, pentyl, hexyl, octyl, nonyl, decyl, cyclohexyl, 2-ethylhexyl, or 1,1-diisopropyl-2-methylpropyl, preferably tert-butyl or 1,1-diisopropyl-2-methylpropyl. The number of —C(=O)X groups to be contained in the cyclic skeletal part of the compound (A) is generally in the range of 2 to 6, preferably 2 to 4, although it is varied with the structure of the cyclic skeletal part constructing the compound (A) and the kind of the —C(=O)X group. Though the positions at which the —C(=O)X groups are joined to the carbon atoms of the cyclic skeletal part of the compound (A) are not particularly limited, the position (1,4) in benzene, the positions (1,2), (2,3), (2,6), and (1,5) in naphthalene, the positions (4,4') and (3,3') in biphenyl, and the positions (9,10), (2,6), and (1,5) in anthracene may be cited. Among other positions cited above, the position (1,4) in benzene, the positions (2,6) and (1,5) in naphthalene, the position (4,4') in biphenyl, and the positions (9,10), (2,6), and (1,5) in anthracene, namely the positions allowed to assume an axis of symmetry in a molecular configuration, prove particularly advantageous. More specifically, the examples of the compound (A) which may be preferably used herein are as follows:

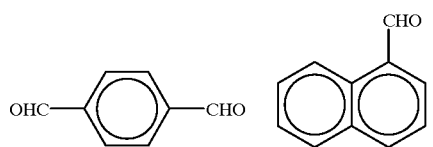

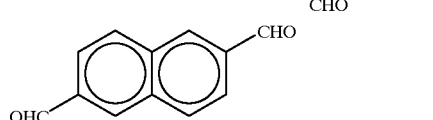

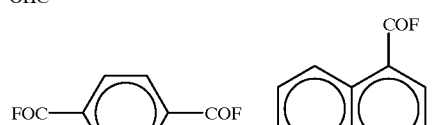

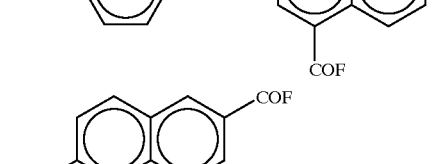

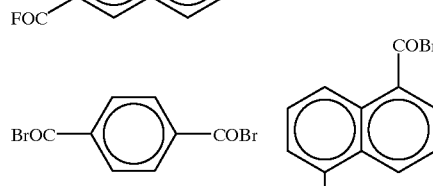

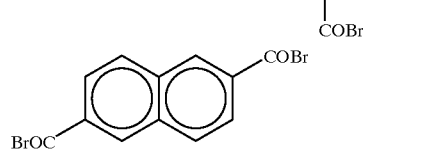

-continued

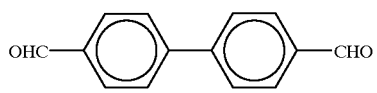

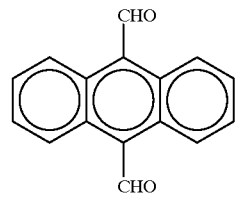

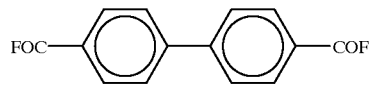

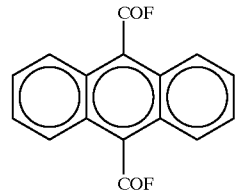

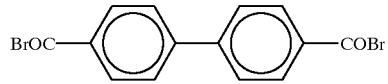

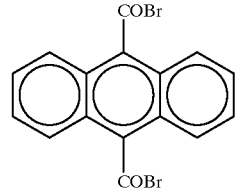

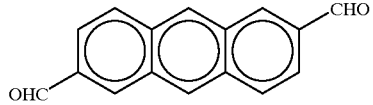

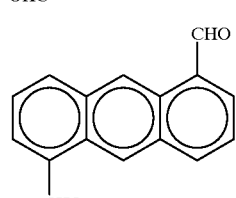

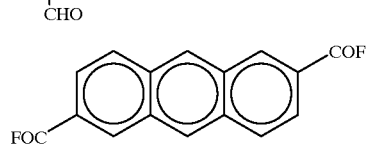

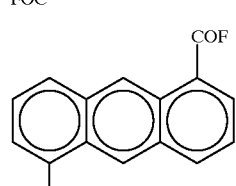

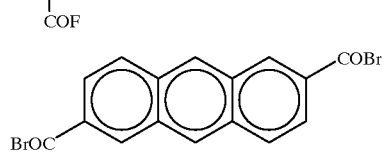

-continued

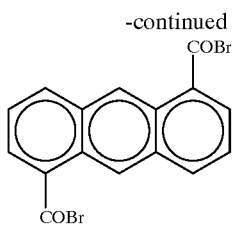

The hydrogen atoms which directly bind to the cyclic skeletal part of the compound (A) except for the —C(=O)X groups may be unsubstituted or partly or wholly substituted with at least one species of halogen atom. The halogen atoms as the substituent may be fluorine, chlorine, bromine, or iodine, preferably fluorine, chlorine, or bromine, and more preferably fluorine. The halogens which are involved in the substitution may be either identical or different with one another. Examples of the compound (A) according to this embodiment which may be particularly used in this invention are as following:

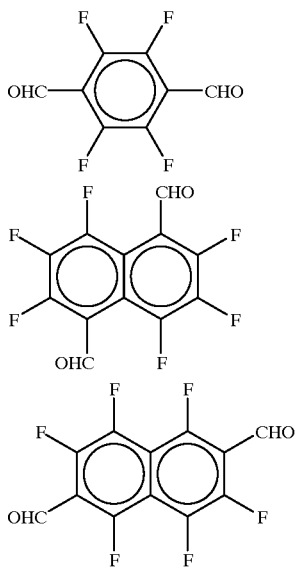

The compound (B) to be used in this invention may be any of the compounds represented by the formula:

wherein $R^1$ and $R^2$ independently represent an alkyl group of 1 to 6, preferably 1 to 3, carbon atoms such as, for example, methyl, ethyl, n-propyl, isopropyl, n-butyl, tert-butyl, pentyl and hexyl, or a phenyl group. In the compounds (B) represented by the formula mentioned above, diethylaminosulfur trifluoride [$(C_2H_5)_2NSF_3$] (hereinafter referred to briefly as "DAST") which has ethyl for both $R^1$ and $R^2$ in the formula mentioned above and dimethylaminosulfur trifluoride [$(CH_3)_2NSF_3$] which has methyl for both $R^1$ and $R^2$ are preferably used in this invention in the sense that they excel in reactivity.

According to this invention, the reaction of the compound (A) with the compound (B) results in displacing the —C(=O)X groups in the compound (A) with the fluorine atoms in the compound (B) and consequently forming a di- or tri-fluoroalkyl group. With consideration for the suitability of the product of reaction for use as the raw material for a heat-resistant resin, the reaction is preferred to form a difluoroalkyl group.

The amount of the compound (B) to be used imposes no particular restriction and only requires to permit efficient reaction with the compound (A). It is generally in the range of 1.2 to 3.0 mol equivalents, preferably 1.5 to 2.5 mol equivalents, based on the amount of the compound (A) used. If the amount of the compound (B) to be used is less than 1.2 mol equivalents, the reaction of the compound (A) with the compound (B) will not proceed thoroughly and the fluorine-containing aromatic compound aimed at by the reaction will be produced in a low yield. Conversely, if the amount of the compound (B) to be used exceeds 3.0 mol equivalents, the excess will make no due addition to the yield with which the fluorine-containing aromatic compound aimed at is produced and will prove unfavorable from the viewpoint of economy because it increases the amount of the compound (B) suffered to remain in an unaltered form and the purification of the product of reaction consumes much time and labor. The term "mol equivalent" as used herein referred to the numerical value calculated by the following formula:

$$\text{Mol equivalent} = [\text{Number of mols of the compound } (B)] /$$
$$\{[\text{Number of mols of the compound } (A)] \times$$
$$[\text{Number of } -C(=O)X \text{ groups in the compound } (A)]\}$$

One embodiment of the method for the production of a fluorine-containing aromatic compound according to this invention will be described below. First, a three-neck flask is vacuumized and then filled with such an inert gas as argon gas or helium gas to deprive the flask interior of the water content such as moisture. Further, the flask is charged with a compound (B) and a solvent to prepare a solution of compound (B). In this case, the compound (B) and the solvent may be mixed in advance and then introduced in a mixed state into the flask or alternatively they may be introduced separately of each other into the flask and then mixed inside the flask. Subsequently, this solution of compound (B) is stirred at a temperature lower than the reaction temperature and the compound (A) which has been dissolved in a solvent is added to the stirred solution. At this time, the solution of compound (A) may be added either collectively or dropwise. Further, the mixed solution is continuously stirred at a humidity (water content) falling within a prescribed range and at a prescribed reaction temperature, to effect the reaction of the compound (A) with the compound (B).

In this invention, the compound (A) and the compound (B) can be directly reacted with each other by being mixed (stirred) instead of performing such a preliminary mixture as is depicted in the embodiment described above. It, however, is preferable for the compound (A) and the compound (B) to be mixed prior to their reaction at a temperature lower by at least 2° C., more preferably at least 5° C., and most preferably at least 15° C., than the reaction temperature until attaining an uniform mixture. If the compound (A) and the compound (B) are mixed and caused to react at a temperature equal to or higher than their reaction temperature, the disadvantage ensues that they would generate heat excessively, promote self-decomposition of the compound (B), and lower the yield of the product aimed at.

The reaction conditions according to this invention are as follows. The reaction temperature is preferred to be a temperature which is lower than the decomposition temperature of the compound (B) and allows the reaction to proceed efficiently. It is generally in the range of 0° to 50° C., preferably in the range of 5° to 30° C. The reaction temperature can be controlled within the range mentioned above by such a process as of dipping the reaction vessel in a refrigeration medium, introducing into the reaction vessel a stream of an inert gas like argon gas or helium gas cooled as with liquid nitrogen, or bubbling the inert gas through the reaction solution. The reaction time is generally in the range of 1 to 24 hours, preferably in the range of 1 to 8 hours.

The reaction of the compound (A) with the compound (B) according to this invention is preferably carried out in an atmosphere in which the water content of the gaseous phase is not more than 100 vol.ppm, more preferably not more than 60 vol.ppm, and most preferably not more than 20 vol.ppm. If the compound (A) and the compound (B) are caused to react in an atmosphere in which the water content of the gaseous phase exceeds 100 vol.ppm, the disadvantage arises that they will promote self-decomposition of the compound (B) and lower the yield of the product aimed at. The water content of the gaseous phase during the course of the reaction of the compound (A) with the compound (B) can be maintained within the range mentioned above by sealing the flask tightly or introducing into the flask such an inert gas as argon gas or helium gas which has been dried by being passed through liquid nitrogen.

In the embodiment as described above, the material for the reaction vessel such as a three-neck flask imposes no particular restriction but only requires to be incapable of reacting with (fluorinating) the compounds (A) and (B) and the solvent. As typical examples of the material, glass, polyethylene, polypropylene, and fluorine resin may be cited. With consideration of the necessity for precluding contamination by elution of alkali metal ions or heavy metal ions, polyethylene, polypropylene, and fluorine resin may be preferably used.

While the embodiment, as depicted above, uses a solvent, the present invention allows each the compound (A) and the compound (B) to be used either in intact form or as dissolved in a solvent. For the purpose of allowing the reaction to proceed efficiently and improving the yield of the product, however, it is preferable for the compounds (A) and (B) to be dissolved in a suitable solvent.

This invention does not discriminate the solvent to be used therein on account of its kind so long as the solvent itself is incapable of being fluorinated. As typical examples of the solvent which is used advantageously herein, aliphatic or aromatic hydrocarbons such as pentane, hexane, octane, and xylene; halogen-containing aliphatic or aromatic hydrocarbons such as dichloromethane, chloroform, 1,2-dichloroethane, 1,1,2,2-tetrachloroethane, carbon tetrachloride, trichlorofluoromethane, and chlorotoluene; and diglyme, and tetrahydrofuran may be cited. Among other solvents cited above, dichloromethane, chloroform, and 1,2-dichloroethane may be used particularly advantageously. For the purpose of improving the efficiency of the reaction, the solvents mentioned above are preferred to be subjected to the known dehydrogenating treatment before they are put to use in the reaction of this invention.

When the solvent is used in this invention, this invention imposes no particular restriction on the amount of the solvent to be used. In consideration of the yield of the reaction and the cost of production, however, the amount of the solvent is preferred to be such that the concentration of the compound (A) in the reaction solution [compound (A)+compound (B)+solvent] may fall within the range of 1 to 30% by weight, preferably 3 to 20% by weight.

The solvent may be mixed in advance with the raw material [compound (A) or compound (B)] and then added to the reaction vessel or alternatively it may be added together with the raw material [compound (A) or compound (B)] to the reaction vessel while stirred.

After the reaction of the compound (A) with the compound (B) described above has been completed, the fluorine-containing aromatic compound aimed at can be separated and purified from the reaction solution (i.e., the solution having undergone the reaction until completion) by subjecting this reaction solution to such a well-known treatment as extraction, separation, and concentration. Alternatively, the fluorine-containing aromatic compound aimed at may be separated and purified from the reaction solution by such known means as silica gel or reversed-phase column chromatography, thin-layer chromatography (TLC), distillation, and recrystallization.

The yield of the target product obtained by the method of this invention can be calculated and rated by subjecting the reaction solution to gas chromatographic (GC) analysis using a flame ionization detector. The use of this procedure allows the content of the target product to be found in terms of peak strength which is proportional to the number of carbon atoms. It also allows the analysis to be attained quantitatively because the peak strength is proportional to the content of the target product for a fixed number of carbon atoms. In the present specification, the ratio of the amount of the by-product (referred to as "product 1" in the following examples) to that of the target product (referred to as "product 2" in the following examples) is calculated by using a peak area which is proportional to a peak strength thereby rating the yield of the fluorine-containing aromatic compound as a target product.

Now, the present invention will be described by reference to working examples and controls below.

The yields of the target products obtained in the following examples and controls are calculated based on the same calculation as described above.

EXAMPLE 1

A three-neck glass flask (reaction vessel), 100 ml in inner volume, was tightly sealed, vacuumized to 10 mmHg by means of a vacuum rotary pump, and then filled with argon gas (water content of 18 vol.ppm) to normal pressure (an ambient pressure). Then, the three-neck flask was fitted with a stirrer as kept swept with argon gas and was charged with 5.06 g (0.0314 mol) of DAST (produced by Aldrich Chemical Co., Inc.) as a compound (B) and 10 ml of dichloromethane (produced by Kanto Chemical Co., Inc.) to prepare a solution of compound (B).

The three-neck flask was dipped in ice water at 1.0° C. and kept at this temperature and a solution of compound (A) obtained by dissolving 1.06 g (0.00789 mol) of terephthalaldehyde (produced by Tokyo Kasei Organic Chemicals and referred to briefly as "TPA" hereinafter) as a compound (A) in 15 ml of dichloromethane was drip-fed into the solution of compound (B) as kept stirred through a dropping funnel over a period of five minutes. In this Example, the amount of the compound (B) used was 2.0 mol equivalents based on the amount of the compound (A) used.

Subsequently, the mixture formed in the flask was stirred continuously at 23° C. under normal pressure for five hours while an argon gas was flowed in the flask at a rate of 5 ml/min, to produce an orange-red reaction solution. The GC-MS (gas chromatography-mass spectrometry) analysis of the resultant reaction solution confirmed the formation therein of 4-difluoromethyl benzaldehyde (product 1) and 1,4-bis(difluoromethyl)benzene (product 2). The GC analysis separately performed on the same sample indicated the area ratio of product 1 to product 2 to be 7/93. By subjecting the reaction solution to separation and purification by means of silica gel column chromatography, 0.91 g (yield 65%) of 1,4-bis(difluoromethyl)benzene was obtained as a product aimed at.

EXAMPLE 2

The reaction of a compound (A) with a compound (B) was attained by following the procedure of Example 1 while changing the amount of DAST as the compound (B) to 2.17 g (0.0135 mol), using 5 ml of toluene in place of 10 ml of dichloromethane, and using as the solution of compound (A) a solution of 0.50 g (0.00271 mol) of 2,3-naphthalenedicarbaldehyde $[C_{10}H_6(CHO)_2$, produced by Aldrich Chemical Co., Inc., hereinafter referred to briefly as "NDA"] in 5 ml of dichloromethane. In this Example, the amount of the compound (B) used was 2.5 mol equivalents based on the amount of the compound (A) used.

When the reaction solution was subjected to GC-MS analysis in the same manner as in Example 1, it was confirmed to have formed therein 2-difluorometyl-3-formylnaphthalene (product 1) and 2,3-bis(difluorometyl)naphthalene (product 2). The GC analysis separately performed in the same manner as in Example 1 indicated the area ratio of product 1 to product 2 to be 5/95.

EXAMPLE 3

The reaction of a compound (a) with a compound (B) was performed by following the procedure of Example 1 except changing the amount of DAST as the compound (B) to 4.83 g (0.030 mol) and using as the solution of compound (A) a solution of 1.34 g (0.01 mol) of TPA as the compound (A) in 30 ml of dichloromethane. In this Example, the amount of the compound (B) used was 1.5 mol equivalents based on the amount of the compound (A) used.

When the reaction solution was subjected to GC-MS analysis in the same manner as in Example 1, it was confirmed to have formed therein 4-difluoromethylbenzaldehyde (product 1) and 1,4-bis(difluoromethyl)benzene (product 2). The GC analysis separately performed in the same manner as in Example 1 indicated the area ratio of product 1 to product 2 to be 25/75.

EXAMPLE 4

The reaction of a compound (a) with a compound (B) was performed by following the procedure of Example 1 except changing the amount of DAST as the compound (B) to 4.86 g (0.0302 mol) and using as the solution of compound (A) a solution of 2.02 g (0.015 mol) of TPA as the compound (A) in 30 ml of dichloromethane. In this Example, the amount of the compound (B) used was 1.0 mol equivalent based on the amount of the compound (A) used.

When the reaction solution was subjected to GC-MS analysis in the same manner as in Example 1, it was confirmed to have formed therein 4-difluoromethylbenzaldehyde (product 1) and 1,4-bis(difluoromethyl)benzene (product 2). The GC analysis separately performed in the same manner as in Example 1 indicated the area ratio of product 1 to product 2 to be 73/27.

REFERENTIAL EXAMPLE 1

Synthesis of 2,6-diformyl naphthalene 2,6-Naphthalene dicarbonyl chloride was synthesized by causing 2,6-naphthalene dicarboxylic acid to react with thionyl chloride by adopting experimental example 5.48 from Shin-jikken Kagaku Koza [sic.] (Vol. 14, page 1107, Maruzen Co., Ltd.).

Example 5.48 ot Shin-jikken Kagaku Koza [sic.] describes the synthesis of ethylphenylacetic acid chloride (using sulfurous oxychloride) via the following reaction:

A mixture of 23.7 g (0.145 mol) of ehtylphenylacetic acid and 71 g (0.6 mol) of sulfurous oxychloride is refluxed at 112° C for 3 hours. An excess sulfurous oxychloride is removed under reduced pressure and the distillation is continued, to obtain a desired acid chloride, produced in an amount of 25 g (Yield of 94%). bp: 112–115° C./15mmHg.

When an acid chloride is to be synthesized from isocrotonic acid, the use of sulfurous oxychloride as a reagent is most preferable. The use of another reagent by-produces a trans-isomer.

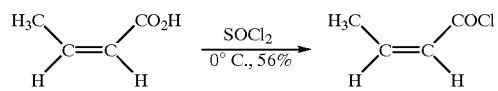

Although a strong acid like trihalogen acid is converted into an acid chloride using solely sulfurous oxychloride with difficulties, the addition of dimethylformamide can product a desired product at a high yield. For example, an acid chloride is produced from trifluoroacetic acid at a yield of 89%.

Then, a solution C was prepared by dissolving 10.9 g (43 m.mols) of the 2, 6-naphthalene dicarbonyl chloride synthesized as described above in 50 ml of acetone. Separately, a solution D was prepared by dissolving 27.4 g (45 m.mols) of Bis (triphenylphosphine) copper (I) tetrahydroborate (produced by Tokyo Kasei Organic Chemicals) in 150 ml of acetone. Then, the solution D was added to the solution C prepared as described above at a rate of 10 ml/min while the solution C was stirred, and the mixed solution was continuously stirred for additional two hours. By extracting the reaction solution from diethyl ether, 5.0 g of 2,6-diformyl naphthalene was obtained (yield: 63%).

EXAMPLE 5

A three-neck glass flask, 100 ml in inner volume, was tightly sealed, vacuumized to 1 mmHg using a vacuum rotary pump, and then filled with argon gas (water content of 18 vol.ppm) to normal pressure (an ambient pressure). Then, the three-neck flask was fitted with a stirrer as kept swept with argon gas and was charged with 9.3 g (0.058 mol) of DAST (produced by Aldrich Chemical Co., Inc.) as a compound (B) and 20 g of dichloromethane to prepare a solution of compound (B).

Then, the three-neck flask was dipped in ice water at 0° C. At the time when the internal temperature thereof reached 0° C., it was maintained at this temperature and the solution of compound (A) of 3.0 g (0.016 mol) of the 2,6-diformyl naphthalene obtained in Reference Example 1 in 30 g of dichloromethane was drip-fed into the solution of compound (B) as kept stirred through a dropping funnel over a period of five minutes. In this Example, the amount of the compound (B) used was 1.8 mol equivalents based on the amount of the compound (A) used.

Subsequently, the mixture formed in the flask was stirred continuously at 30° C. under normal pressure for six hours while an argon gas was flowed in the flask at a rate of 5 ml/min, to produce an orange-red reaction solution. When the reaction solution was subjected to GC-MS analysis in the same manner as in Example 1, it was confirmed to have formed therein 2-formyl-6-difluoromethyl naphthalene (product 1) and 2,6-difluoromethyl naphthalene (product 2). The GC analysis separately performed in the same manner as in Example 1 indicated the area ratio of product 1 to product 2 to be 10/90.

The results of Examples 1 to 5 are collectively shown in Table 1 given below.

TABLE 1

| Example | Compound (A) | Compound (B) | B/A (Mol equivalent) | Product 1 | Product 2 |
|---|---|---|---|---|---|
| 1 | TPA 1.06 g (0.00789 mol) | DAST 5.06 g (0.0314 mol) | 2.0 | 7 | 93 |
| 2 | TPA 0.05 g (0.00271 mol) | DAST 2.17 g (0.0135 mol) | 2.5 | 5 | 95 |
| 3 | TPA 1.34 g (0.01 mol) | DAST 4.83 g (0.030 mol) | 1.5 | 25 | 75 |
| 4 | TPA 2.02 g (0.015 mol) | DAST 4.86 g (0.0302 mol) | 1.0 | 73 | 27 |
| 5 | 2,6-diformyl naphthalene 3.0 g (0.016 mol) | DAST 9.3 g (0.058 mol) | 1.8 | 10 | 90 |

TPA: Terephthalaldehyde
NDA: 2,3-Naphthalenedicarbaldehyde
DAST: Diethylaminosulfur trifluoride
B/A: This numerical value calculated by the formula: [Number of mols of the compound (B)]/{[Number of mols of the compound (A)] × [Number of —C(=O)X groups in the compound (A)]}
Reaction time: 5 hours in Examples 1 to 4; 6 hours in Example 5
Reaction temperature: 23° C. in Examples 1 to 4; 30° C. in Example 5
Solvent: CH$_2$Cl$_2$ or toluene It is clearly noted from Table 1 that when the amount of the compound (B) used is set to be less than 1.2 mol equivalents based on the amount of the compound (A) used, the disadvantages arise that the reaction would rapidly form a by-product (product 1) and the yield of the target product (product 2) would be unduly lowered. On the other hand, when the amount of the compound (B) used is set to exceed 3.0 mol equivalents based on the amount of the compound (A) used, the disadvantages similarly ensue that the yield of the target product (product 2) would not increase and the amount of the compound (B) suffered to remain in an unaltered form would be unduly large. These results clearly indicate that the amount of the compound (B) used is preferably fallen within the range of 1.2 to 3.0 mol equivalents based on the amount of the compound (A) used.

Further, according to the methods of the present Examples, the reaction for fluorination can be simply carried out at room temperature under an ambient pressure and DAST to be used as a raw material exhibits appreciably low corrosiveness as compared with sulfur tetrafluoride which has been conventionally used. Therefore, the method of this invention obviates the necessity of using a reaction vessel made of such a special material as has been found necessary heretofore or adopting harsh reaction conditions and instead permits use of a reaction vessel made of such an ordinary material as glass. Furthermore, the fluorine-containing aromatic compound aimed at can be manufactured safely at low costs because DAST has low toxicity.

The entire disclosure of Japanese Patent Application No. 09-235149 filed on Aug. 29, 1997 including specification, claims, drawings and summary are incorporated herein by reference in its entirety.

We claim:

1. A method for the production of a fluorine-containing aromatic compound which comprises reacting an aromatic compound (A) having a cyclic skeletal part of 6 to 16 carbon atoms with a plurality of —C(=O)X groups, wherein X stands for a hydrogen atom, a halogen atom, or an alkyl group of 1 to 10 carbon atoms, and having the remaining hydrogen atoms unsubstituted or partly or wholly substituted with at least one species of halogen atom to react with a compound (B) represented by the formula:

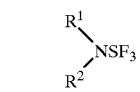

wherein R$^1$ and R$^2$ independently stand for an alkyl group of 1 to 6 carbon atoms or a phenyl group, the amount of said compound (B) used being in the range of 1.2 to 3.0 mol equivalents based on the amount of the compound (A) used.

2. A method according to claim 1, wherein said cyclic skeletal part is benzene, naphthalene, or biphenyl.

3. A method according to claim 1, wherein said halogen for substituting the remaining hydrogen atom is fluorine, chlorine, or bromine.

4. A method according to claim 3, wherein said halogen for substituting the remaining hydrogen atom is fluorine.

5. A method according to claim 1, wherein the amount of said compound (B) used is in the range of 1.5 to 2.5 mol equivalents based on the amount of the compound (A) used.

6. A method according to claim 1, wherein said compound (A) and said compound (B) are preliminarily mixed at a temperature lower than the reaction temperature prior to the reaction of the compound (A) with the compound (B).

7. A method according to claim 6, wherein said compound (A) and said compound (B) are preliminarily mixed at a temperature lower by at least 2° C. than the reaction temperature prior to the reaction of the compound (A) with the compound (B).

8. A method according to claim 1, wherein the reaction of said compound (A) with said compound (B) is carried out in an atmosphere in which the water content of the gaseous phase is not more than 100 vol.ppm.

9. A method according to claim 8, wherein the reaction of said compound (A) with said compound (B) is carried out in an atmosphere in which the water content of the gaseous phase is not more than 60 vol. ppm.

10. A method according to claim 9, wherein the reaction of said compound (A) with said compound (B) is carried out in an atmosphere in which the water content of the gaseous phase is not more than 20 vol. ppm.

* * * * *